US00PP32886P2

(12) United States Plant Patent
Geibel

(10) Patent No.: US PP32,886 P2
(45) Date of Patent: Mar. 9, 2021

(54) ***PELARGONIUM* PLANT NAMED 'PACVINT'**

(50) Latin Name: *Pelargonium peltatum*
Varietal Denomination: Pacvint

(71) Applicant: ELSNER pac JUNGPFLANZEN GbR, Thiendorf (DE)

(72) Inventor: Martin Geibel, Dresden (DE)

(73) Assignee: ELSNER pac JUNGPFLANZEN GbR, Thiendorf (DE)

( * ) Notice: Subject to any disclaimer, the term of this patent is extended or adjusted under 35 U.S.C. 154(b) by 0 days.

(21) Appl. No.: 16/873,682

(22) Filed: Jun. 1, 2020

(51) Int. Cl.
*A01H 6/42* (2018.01)
*A01H 5/02* (2018.01)

(52) U.S. Cl.
USPC ..... Plt./332

(58) Field of Classification Search
USPC ..... Plt./332
See application file for complete search history.

*Primary Examiner* — Annette H Para
(74) *Attorney, Agent, or Firm* — C. Anne Whealy

(57) ABSTRACT

A new and distinct Ivy Geranium plant named 'Pacvint', characterized by its mounding, upright to trailing and cascading plant habit; moderately vigorous growth habit; freely basal branching habit; medium green-colored leaves; early and freely flowering habit; red purple semi-double flowers that are held above and beyond the foliar plane on strong peduncles; and good high temperature tolerance.

1 Drawing Sheet

Botanical designation: *Pelargonium peltatum.*
Cultivar denomination: 'PACVINT'.

BACKGROUND OF THE INVENTION

The present invention relates to a new and distinct cultivar of Ivy Geranium plant, botanically known as *Pelargonium peltatum*, and hereinafter referred to by the cultivar name 'Pacvint'.

The new Ivy Geranium plant is a product of a planned breeding program conducted by the Inventor in Dresden, Germany. The objective of the breeding program is to develop new uniform and early-flowering Ivy Geranium plants with numerous attractive flowers.

The new Ivy Geranium plant originated from a cross-pollination made by the Inventor of two unidentified proprietary selections of *Pelargonium grandiflorum*, not patented, during the summer of 2014. Seed was collected from a number of potential parent plants, combined and sown. The new Ivy Geranium plant was discovered and selected by the Inventor as a single flowering plant from within the progeny of the stated mass cross-pollination in a controlled greenhouse environment in Dresden, Germany during the spring of 2015.

Asexual reproduction of the new Ivy Geranium plant by vegetative terminal cuttings in a controlled greenhouse environment in Dresden, Germany since December, 2015 has shown that the unique features of this new Ivy Geranium plant are stable and reproduced true to type in successive generations.

SUMMARY OF THE INVENTION

Plants of the new Ivy Geranium have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Pacvint'. These characteristics in combination distinguish 'Pacvint' as a new and distinct Ivy Geranium plant:

1. Mounding, upright to trailing and cascading plant habit.
2. Moderately vigorous growth habit.
3. Freely basal branching habit.
4. Medium green-colored leaves.
5. Early and freely flowering habit.
6. Red purple semi-double flowers that are held above and beyond the foliar plane on strong peduncles.
7. Good high temperature tolerance.

Plants of the new Ivy Geranium can be compared to plants of the *Pelargonium peltatum* 'Pacpisyb', disclosed in U.S. Plant Pat. No. 21,849. In side-by-side comparisons, plants of the new Ivy Geranium differ from plants of 'Pacpisyb' in the following characteristics:

1. Plants of the new Ivy Geranium are smaller than plants of 'Pacpisyb'.
2. Flowers and flower petals of plants of the new Ivy Geranium are larger than flowers and flower petals of plants of 'Pacpisyb'.
3. Flowers of plants of the new Ivy Geranium are darker red purple in color than flower of plants of 'Pacpisyb'.
4. Plants of the new Ivy Geranium have shorter peduncles than plants of 'Pacpisyb'.

BRIEF DESCRIPTION OF THE PHOTOGRAPH

The accompanying colored photograph illustrates the overall appearance of the new Ivy Geranium plant showing the colors as true as it is reasonably possible to obtain in colored reproductions of this type. Colors in the photograph may differ slightly from the color values cited in the detailed botanical description which accurately describe the colors of the new Ivy Geranium plant. The photograph comprises a side perspective view of a typical flowering plant of 'Pacvint' grown in a container.

DETAILED BOTANICAL DESCRIPTION

The aforementioned photograph and following observations, measurements and values describe plants grown in 19-cm containers during the spring, summer and autumn in a glass-covered greenhouse in Dresden, Germany and under cultural practices typical of commercial Ivy Geranium production. During the production of the plants, day temperatures ranged from 18° C. to 20° C., night temperatures averaged 18° C. and light levels ranged from 15 klux to 100 klux. Plants were pinched two times and were nine months old when the photograph and the detailed description were taken. In the following detailed description, color references are made to The Royal Horticultural Society Colour Chart, 1995 Edition, except where general terms of ordinary dictionary significance are used.

Botanical classification: *Pelargonium peltatum* 'Pacvint'.

Parentage:

*Female, or seed, parent.*—Unidentified proprietary selection of *Pelargonium peltatum*, not patented.

*Male or pollen parent.*—Unidentified proprietary selection of *Pelargonium peltatum*, not patented.

Propagation:

*Type.*—By vegetative terminal cuttings.

*Time to initiate roots, summer.*—About 18 days at temperatures about 20° C.

*Time to initiate roots, winter.*—About 22 days at temperatures about 20° C.

*Time to produce a rooted young plant, summer.*—About four weeks at temperatures about 20° C.

*Time to produce a rooted young plant, winter.*—About four weeks at temperatures about 18° C.

*Root description.*—Fine, fibrous; typically white in color, actual color of the roots is dependent on substrate composition, water quality, fertilizers, substrate temperature and age of roots.

*Rooting habit.*—Freely branching; dense.

Plant description:

*Plant and growth habit.*—Mounding, upright to trailing and cascading plant habit; densely foliated; moderately vigorous growth habit; rapid growth rate; freely branching habit with about 15 lateral branches per plant; pinching enhances lateral branch development.

*Plant height, to top of umbels.*—About 35 cm.

*Plant height, to top of foliar plane.*—About 25 cm.

*Plant width.*—About 60 cm.

*Lateral branches.*—Length: About 40 cm. Diameter: About 5 mm. Internode length: About 3 cm. Texture: Moderately pubescent. Color, developing and developed: Close to 144A.

Leaf description:

*Arrangement.*—Opposite; simple.

*Length.*—About 4 cm.

*Width.*—About 7 cm.

*Shape.*—Palmately lobed; ivy leaf-shaped.

*Apex.*—Acute.

*Base.*—Cordate, open to imbricate.

*Margin.*—Lobed.

*Venation pattern.*—Palmate.

*Texture, upper and lower surfaces.*—Slightly pubescent, coriaceous.

*Color.*—Developing and fully expanded leaves, upper surface: Close to 137A; venation, close to 137A; no zonal discernible pattern. Developing and fully expanded leaves, lower surface: Close to 146B; venation, close to 144A.

*Petioles.*—Length: About 4 cm. Diameter: About 2 mm. Texture, upper and lower surfaces: Pubescent; rough. Color, upper and lower surfaces: Close to 144A.

Flower description:

*Flower arrangement and flowering habit.*—Semi-double flowers arranged in roughly hemispherical umbels arising from apical leaf axils; umbels displayed above and beyond the foliar plane on strong peduncles; flowers face mostly upright to outwardly depending on position in the umbel; freely flowering habit with about six open flowers per umbel and numerous umbels developing per plant during the flowering season.

*Fragrance.*—None detected.

*Flowering season.*—Early flowering habit; plants begin flowering about 105 days after planting; in the garden in Germany, flowering begins in May and continues until frost in the autumn.

*Flower longevity.*—Flowers last about six to ten days on the plant; umbels last about three to four weeks on the plant; flowers persistent.

*Umbel height.*—About 5 cm.

*Umbel diameter.*—About 9 cm.

*Flower diameter.*—About 5 cm.

*Flower depth (height).*—About 2 cm.

*Flower buds.*—Length: About 1 cm. Diameter: About 6 mm. Shape: Elliptic to rounded. Color: Close to 144A.

*Petals.*—Quantity per flower: About 19 in several whorls; petals imbricate. Length, upper petals: About 2.9 cm. Length, lower petals: About 2.6 cm. Width, upper petals: About 1.8 cm. Width, lower petals: About 1.9 cm. Shape: Obovate. Apex: Rounded. Base: Cuneate. Margin: Entire. Texture, upper and lower surfaces: Smooth, glabrous; velvety. Color: When opening and fully opened, upper surface: Close to 57A; towards the base, close to 155D; venation, close to 60A; color becoming closer to 66B with development. When opening and fully opened, lower surface: Close to 65B; towards the base, close to 155D; venation, close to 60B; color does not change with development.

*Petaloids.*—Quantity per flower: About two to five at the center of the flower. Length: About 1 cm to 1.5 cm. Width: About 5 mm to 15 mm. Shape: Irregular, roughly obovate. Apex: Rounded. Base: Cuneate. Margin: Entire. Texture, upper and lower surfaces: Rugose, glabrous; velvety. Color: When opening and fully opened, upper surface: Close to 57A; towards the base, close to 155D; venation, close to 60A; color becoming closer to 66B with development. When opening and fully opened, lower surface: Close to 65B; towards the base, close to 155D; venation, close to 60B; color does not change with development.

*Sepals.*—Quantity per flower: Five arranged in a single whorl; not fused. Length: About 1.3 cm. Width:

About 4 mm. Shape: Lanceolate. Apex: Acute. Base: Truncate. Margin: Entire. Texture, upper and lower surfaces: Slightly pubescent. Color, upper and lower surfaces: Close to 144A.

*Peduncles* (*umbel stems*).—Length: About 11 cm. Diameter: About 3 mm. Strength: Strong. Angle: Upright to outwardly. Texture: Slightly pubescent. Color: Close to 144A.

*Pedicels* (*individual flower stems*).—Length: About 2.2 cm. Diameter: About 2 mm. Strength: Moderately strong; flexible. Texture: Slightly pubescent. Color: Close to 144A.

*Reproductive organs*.—Androecium: Stamen quantity per flower: About eight. Anther length: About 2 mm. Anther shape: Tubular. Anther color: Close to 200A. Pollen amount: None observed. Gynoecium: Pistil quantity per flower: One. Pistil length: About 1.1 cm. Stigma shape: Five or six-parted. Stigma color: Close to 187A. Style length: About 4 mm. Style color: Close to 155D. Ovary color: Close to 139D. Seeds and fruits: To date, seed and fruit development have not been observed on plants of the new Ivy Geranium.

Pathogen & pest resistance: To date, plants of the new Ivy Geranium have not been observed to be resistant to pathogens and pests common to Ivy Geranium plants.

Temperature tolerance: Plants of the new Ivy Geranium have been observed to tolerate temperatures ranging from about 0.5° C. to about 40° C.

It is claimed:

1. A new and distinct Ivy Geranium plant named 'Pacvint' as illustrated and described.

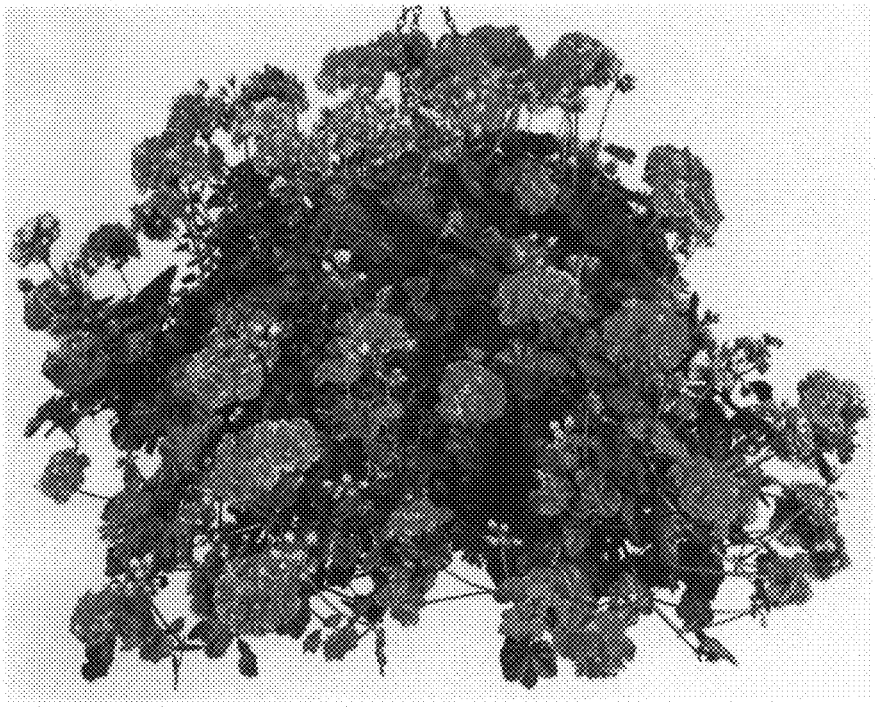

* * * * *